United States Patent
Wiss et al.

(10) Patent No.: US 8,066,798 B2
(45) Date of Patent: Nov. 29, 2011

(54) METHOD FOR SELECTING A GAS FILTERING STRUCTURE

(75) Inventors: Celine Wiss, Caumont sur Durance (FR); Patrick Jacques Dominique Girot, Salon de Provence (FR)

(73) Assignee: Saint-Gobain Centre de Recherches et d'Etudes European, Courbevoie (FR)

( * ) Notice: Subject to any disclaimer, the term of this patent is extended or adjusted under 35 U.S.C. 154(b) by 527 days.

(21) Appl. No.: 12/095,071

(22) PCT Filed: Nov. 29, 2006

(86) PCT No.: PCT/FR2006/051255
§ 371 (c)(1),
(2), (4) Date: Sep. 16, 2008

(87) PCT Pub. No.: WO2007/063250
PCT Pub. Date: Jun. 7, 2007

(65) Prior Publication Data
US 2009/0301047 A1    Dec. 10, 2009

(30) Foreign Application Priority Data
Nov. 30, 2005   (FR) ..................................... 05 53666

(51) Int. Cl.
*B01D 46/00*    (2006.01)
(52) U.S. Cl. ................. 95/1; 55/523; 55/DIG. 5; 95/273
(58) Field of Classification Search ............ 55/522–524; 422/169–172, 177–182; 60/297
See application file for complete search history.

(56) References Cited

U.S. PATENT DOCUMENTS

| | | | | |
|---|---|---|---|---|
| 4,783,751 A | * | 11/1988 | Ehrlich et al. ................... 702/11 |
| 5,787,208 A | * | 7/1998 | Oh et al. ........................ 382/257 |
| 5,851,649 A | * | 12/1998 | Mohri et al. ................ 428/319.1 |
| 2003/0110744 A1 | * | 6/2003 | Gadkaree et al. ................ 55/523 |
| 2003/0165662 A1 | * | 9/2003 | Suwabe et al. ................. 428/116 |
| 2006/0107641 A1 | * | 5/2006 | Kasai et al. ...................... 55/523 |
| 2006/0112669 A1 | * | 6/2006 | Yamada et al. ................... 55/523 |
| 2006/0174695 A1 | * | 8/2006 | Miyashita et al. ................. 73/38 |
| 2007/0033912 A1 | * | 2/2007 | Furukawa et al. ............... 55/523 |
| 2007/0119133 A1 | * | 5/2007 | Beall et al. ....................... 55/523 |

FOREIGN PATENT DOCUMENTS

| | | |
|---|---|---|
| EP | 0 778 250 | 6/1997 |
| EP | 1 316 686 | 6/2003 |
| EP | 1 607 734 | 12/2005 |
| EP | 1 655 274 | 5/2006 |
| JP | 8-28246 A | 1/1996 |
| JP | 2004-360654 A | 12/2004 |
| JP | 2005-511294 T | 4/2005 |
| WO | WO 2004/046063 A1 | 6/2004 |
| WO | WO 2005/009922 A1 | 2/2005 |

OTHER PUBLICATIONS

Japanese Office Action issued on Nov. 2, 2010 in corresponding Japanese Application No. 2008-542811 (English Translation Only).

* cited by examiner

*Primary Examiner* — Jason M Greene
*Assistant Examiner* — Amber Orlando
(74) *Attorney, Agent, or Firm* — Oblon, Spivak, McClelland, Maier & Neustadt, L.L.P.

(57) ABSTRACT

A method for selecting a filtering structure for a gas laden with particulates, said structure comprising a filtering part formed from a porous ceramic material and comprising at least one, and preferably a plurality, of porous walls, said method being characterized in that, starting from a first image of the surface of the wall, a processing operation is carried out on said first image comprising a morphological erosion by a structuring element in such a manner as to obtain a second characteristic image of the regularity and of the uniformity of the microstructure of said wall.

Silicon carbide filtering structure obtained by application of said method.

14 Claims, No Drawings

METHOD FOR SELECTING A GAS FILTERING STRUCTURE

The present application is the U.S. counterpart of WO 07/063,250, the text of which is incorporated by reference and claims the priority of French application No. 05/53666 filed on Nov. 30, 2005, the text of which is incorporated by reference.

The invention relates to the field of filtering structures, which may comprise a catalytic component, used for example in an exhaust line of an internal combustion engine of the diesel type.

Filters for the treatment of gases and for eliminating soot particles typically coming from a diesel engine are well known in the prior art. These structures usually all have a honeycomb structure, one of the faces of the structure allowing the entry of the exhaust gases to be treated and the other face for exit of the treated exhaust gases. The structure comprises, between the entry and exit faces, an assembly of adjacent ducts or channels, whose axes are parallel to one other, separated by porous walls. The ducts are sealed off at one or other of their ends in order to form inlet chambers opening onto the entry face and outlet chambers opening onto the exit face. The channels are alternately closed off in an order such that, in the course of their passage through the honeycomb body, the exhaust gases are forced to pass through the sidewalls of the inlet channels in order to rejoin the outlet channels. In this way, the particulates or soot particles are deposited and accumulate on the porous walls of the filter body.

Currently, for gas filtration, filters made from a porous ceramic material are used, for example made from cordierite, from alumina, from mullite, from silicon nitride, from a silicon/silicon carbide mixture or from silicon carbide.

In a known manner, during use, the particulate filter is subjected to a succession of filtration (soot accumulation) and regeneration (soot elimination) phases. During the filtration phases, the soot particles emitted by the engine are retained and deposited inside the filter. During the regeneration phases, the soot particles are burnt off inside the filter, in order to restore its filtering properties to it. One important criterion involved in the implementation and the lifetime of a filter, for example in the exhaust line of an engine, is therefore its thermomechanical resistance.

It is furthermore known that the introduction of a particulate filter such as previously described into the exhaust line of an engine leads to a pressure drop likely to impair the performance parameters of the latter. Consequently, the filter must be configured in such a manner as to avoid such an impairment.

Another critical criterion for the selection of the, optionally, catalytic filtering structures previously described is their soot deposition time. This time corresponds to the time period required for the filter to reach its maximum filtering efficiency level, when it is first implemented or following a regeneration phase. It is assumed that this time depends, in particular, on the deposition of a sufficient quantity of soot within the porosity of the filter in order to impede the direct passage of fine soot particles through the walls of the filter. One of the direct consequences of a maladapted soot deposition time is the appearance of persistent and noxious black fumes, together with the presence of traces of soot at the outlet of the exhaust line, on a new filter or after a regeneration phase. It goes without saying that, for reasons of environmental impact, of image and of comfort of use, the automobile manufacturers would like the occurrence of such phenomena to be eliminated or at least minimized on vehicles fitted with such filters.

The deposition of soot is a poorly understood phenomenon, owing without doubt to the fact that the mass of deposited soot is not measurable in real time on a filter during use. Indeed, only the soot deposition time, measured indirectly based on the analysis of the concentration of particulates present in the exhaust gases at the outlet of the filter, is accessible.

The method, subject of the present invention, relates to the field of particulate filters made of porous ceramic material, for example included in the group composed of cordierite, alumina, mullite, silicon nitride, silicon/silicon carbide mixtures and, preferably, silicon carbide.

The application of the invention is particularly suited to the case where the particulate filters are silicon carbide filters, for example obtained by a sintering/recrystallization process (R-SiC). Examples of such catalytic filters are for example described in the patent applications EP 816 065, EP 1 142 619, EP 1 455 923 and WO 2004/065088 to which reference will be made for a more detailed description of their structure or their mode of synthesis. The structures according to the invention may be simple monolithic structures or, preferably, more complex assembled structures, usually obtained by the association of several monolithic elements, bonded by a cement referred to as sealing cement.

The object of the present invention is thus to provide a method allowing honeycomb structures to be selected that are capable of prolonged use as a particulate filter, in other words that allow all of the aforementioned problems to be solved.

More precisely, the present invention relates to a method for selecting a filtering structure for a gas laden with particulates, said structure comprising a filtering part formed from a porous ceramic material and comprising at least one, and preferably a plurality, of porous walls, said method being characterized in that, starting from a first image of the surface of the wall, a processing operation is carried out on said first image comprising a morphological erosion by a structuring element, in such a manner as to obtain a second characteristic image of the regularity and of the uniformity of the microstructure of said wall.

According to one advantageous embodiment, the dimensions and, potentially, the morphology of the structuring element are chosen as a function of the median pore diameter, as measured by mercury porosimetry. The median pore diameter is understood to mean, in the sense of the present description, the pore diameter for which 50% by volume of pores are less than or equal to this pore size.

For example, the structuring element is a disk chosen such that the ratio of its diameter to the median pore diameter is in the range between 1.5 and 5, and preferably between 2.5 and 4.5.

The method according to the invention can, for example, comprise the following steps:
 prepare a section of wall, preferably polished,
 perform an image acquisition, preferably by means of a scanning electron microscope (SEM), preferably in backscattered electron (BSE) mode,
 process the raw images by a thresholding technique in order to obtain digitized images,
 process the digitized images using the morphological erosion technique by means of a structuring element adapted to the median pore size of the filter,
 characterize the remaining regions of porosity,
 select the filtering structures on the basis of at least one of the following criteria:
 a) the number of residual regions remaining after erosion,
 b) the cumulative area of said regions,
 c) the mean area of said regions.

The present method is especially applicable to the porous materials chosen within the group composed of cordierite, alumina, mullite, silicon nitride, silicon/silicon carbide mixtures.

The present method is typically applicable when said walls exhibit an open porosity in the range between 30 and 60%, preferably between 40 and 53%, and more preferably between 44 and 50%, and a median pore diameter in the range between 8 and 30 µm, preferably between 9 and 25 µm, and more preferably between 10 and 18 µm.

The invention thus relates to a filtering structure made from recrystallized silicon carbide (R-SiC) able to be obtained by the method such as previously described and combining, for a maximum filtration efficiency and long-term use, the following properties:
- a minimum pressure drop during operation, typically on an exhaust line of an internal combustion engine,
- an optimized filtering efficiency as soon as the filter is implemented or after a regeneration phase, resulting in a minimized soot deposition time,
- thermomechanical properties sufficient to withstand the operational constraints of the filter.

More particularly, the invention relates to an SiC filtering structure, of the honeycomb type, comprising a filtering part formed from a porous ceramic material with open porosity in the range between 30 and 53%, preferably between 44 and 50%, and whose median pore diameter is in the range between 8 and 20 µm, preferably between 10 and 18 µm, said structure being characterized by at least one, and preferably all, of the following criteria, determined by the application of the method described previously:

a) the number of residual regions remaining after erosion by a structuring element, formed by a disk whose diameter is in the range between 2.5 and 4.5 times the median pore diameter, is less than $100/mm^2$ of wall, and preferably less than $80/mm^2$ of wall, or even less than $50/mm^2$ of wall.

b) the cumulated area of said regions is less than 10,000 $\mu m^2$ per $mm^2$ of wall, and preferably less than 8000 $\mu m^2$ per $mm^2$ of wall, or even less than 5000 $\mu m^2$ per $mm^2$ of wall.

c) the mean area of said regions is less than 400 $\mu m^2$ per $mm^2$ of wall, and preferably less than 200 $\mu m^2$ per $mm^2$ of wall.

The porous material is preferably silicon carbide recrystallized at a temperature in the range between 2100 and 2400° C.

The thickness of the walls of the R-SiC filtering structure according to the invention is in the range between 200 and 500 µm.

Advantageously, the central part of a filter according to the invention comprises a plurality of filtering elements in a honeycomb bonded together by a sealing cement.

For example, the density of channels in the filtering elements is in the range from 7.75 to 62 per $cm^2$, said channels having a cross-section from 0.5 to 9 $mm^2$.

Optionally, the filtering structure according to the invention can comprise a catalytic coating for the treatment of polluting gases of the CO or HC type.

Such a structure may notably be applied as a particulate filter within an exhaust line of a diesel or gasoline engine, preferably of a diesel engine.

The invention and its advantages will be better understood upon reading the non-limiting examples that follow. In the examples, all the percentages are given by weight.

The filters in the following examples were synthesized starting from an initial mixture of the four following constituents:

constituent A: a first powder composed of Sic particles whose median diameter $d_{50}$ varies between 5 and 50 µm, at least 10% by weight of the particles having a diameter greater than 5 µm, constituent B: a second powder composed of Sic particles of median diameter $d_{50}$ in the range between 0.1 and 10 µm, constituent C: a pore-forming agent of the polyethylene type, constituent D: an organic binder of the methyl cellulose type.

EXAMPLE 1

A first particulate filter was synthesized and tested. Firstly, 50 parts by weight of constituent A composed of a powder of Sic particles with median diameter $d_{50}$ of around 30 µm and 50 parts by weight of constituent B with a median diameter of the Sic particles of around 2.5 µm were mixed in a mixture.

Secondly, 5% by weight of constituent C with respect to the total mass of constituents A and B and 5% by weight of constituent D with respect to the total mass of constituents A and B were added to this first mixture.

Water was added and mixing was continued until a uniform paste was obtained whose plasticity allowed it to be extruded through an extrusion die as honeycomb monolithic structures whose dimensional characteristics are given in table 1:

TABLE 1

| | |
|---|---|
| Channel geometry | Square |
| Channel density | 180 cpsi (channels per sq in, 1 inch = 2.54 cm) |
| Wall thickness | 350 µm |
| Length | 15.2 cm |
| Width | 3.6 cm |
| Volume | 2.47 liters |

Subsequently, the green monoliths obtained were dried by microwave for a time sufficient to bring the proportion of water not chemically bound to less than 1% by weight. The channels were alternately closed off on each face of the monolith according to well-known techniques, for example those described in application WO 2004/065088. The monolith was then fired with a temperature rise of 20° C./h until a temperature of around 2200° C. was reached, which was maintained for 2 hours.

A series of silicon carbide monoliths were finally obtained whose microstructural characteristics depended on the composition of the initial mixture and on the synthesis conditions.

The elements coming from one and the same mixture were then assembled together by bonding with a cement of the ceramic type and then machined, in order to form filters of 14.4 cm diameter in accordance with the teaching of patent application EP 816 065. The filters obtained according to this example correspond to specimen 1 in table 2.

EXAMPLES 2 to 5

In these examples, the filter synthesis protocol described in the example 1 was reproduced in an identical manner.

The differences introduced so as to modify the microstructural properties of the monolithic structures obtained were as follows:
various powders whose median particle diameter varied between 5 and 50 µm were used as constituent A, at least 10% by weight of the particles making up these powders having a diameter larger than 5 μm, various powders with median Sic particles diameter varying between 0.1 and 10 μm were used as constituent B, and the proportions of constituents A and B were varied within the following limits:

Constituent A: from 20 to 80%,

Constituent B: from 80 to 20%, in order to obtain a first mixture comprising exclusively (100%) constituents A and B.

Secondly, constituents C and D were then added to each mixture A and B, in proportions ranging from 3 to 12% and 1 to 20% by weight, respectively, with respect to the total mass of constituents A and B.

The dimensional characteristics of the monoliths and of the filters obtained after assembly were identical to those given in example 1.

The specimens thus obtained were evaluated according to three different tests:

A—Measurement of the Soot Deposition Time:

The soot deposition time is the time required for the deposition of a sufficient quantity of soot, on a new filter or following a regeneration, in order for it to reach its maximum level of filtration efficiency.

For the measurement, the filter to be tested was installed on an exhaust line of an engine on a test bench. The engine employed was a Diesel engine with a capacity of 2.0 liters. The filter was progressively loaded with soot by the operation of the engine at a speed of 3000 rpm at 50 Nm.

The bench was equipped with an ELPI (Electrical Low Pressure Impactor) system, known per se, which allowed the particulate concentration in a gas to be measured in real time starting from the moment the filter was loaded. A curve of filtration efficiency as a function of time was thus obtained, this being characterized by a quasi-plateau after a given testing time. The plateau corresponds to a filtration efficiency greater than or equal to 99%. The period of time between the start of the loading of the filter and the time from which an efficiency equal to at least 99% is obtained corresponds, according to the present invention, to the soot deposition time.

B—Measurement of the Pressure Drop:

Pressure drop, within the meaning of the present invention, is understood to mean the differential pressure existing between the upstream side and the downstream side of the filter. The pressure drop was measured according to the techniques of the prior art for an air flow of 300 $m^3/h$ in an ambient air current.

C—Measurement of the Thermomechanical Resistance:

The filters were mounted on an exhaust line of a 2.0 L diesel engine running at full power (4000 rpm) for 30 minutes, then dismantled and weighed in order to determine their initial mass. The filters were then reinstalled on the engine test bench with a speed of 3000 rpm and a torque of 50 Nm for different periods of time in order to obtain a soot load of 5 g/l in the filter.

The filters thus loaded were remounted on the line in order to undergo an intense regeneration defined as follows: after stabilization at an engine speed of 1700 rpm at a torque of 95 Nm for 2 minutes, a post-injection was performed with 70° of phasing for a post-injection flow rate of 18 $mm^3$/stroke. Once the combustion of the soot deposits had been initiated, more precisely when the load loss decreased over a period of at least 4 seconds, the engine speed was reduced to 1050 rpm at a torque of 40 Nm for 5 minutes in order to accelerate the combustion of the soot deposits. The filter was then subjected to an engine speed of 4000 rpm for 30 minutes in order to eliminate the remaining soot.

The regenerated filters are inspected after cutting up in order to reveal the possible presence of cracks visible to the naked eye. The filter is judged to be valid (in other words it exhibits a thermomechanical resistance that is acceptable for use as a particulate filter) if no cracks are visible after this test.

The microstructural characteristics of the samples were subsequently measured by various techniques:

D—Porosimetry of the Material Forming the Walls:

The porosity of the silicon carbide forming the walls was determined according to the conventional high-pressure mercury porosimetry techniques, with a porosimeter of the Micromeritics 9500 type. The analyses show, for all the samples tested, a unimodal distribution of the pore sizes. The median pore diameter was determined using the cumulative pore volume distribution as a function of the pore size, obtained by porosimetry measurement using the mercury porosimeter.

E—Analysis by scanning electron microscopy (SEM) and image processing:

As a first step, a section of wall belonging to each of the samples was prepared by polishing.

Photographs of a surface area of 1 $mm^2$ of wall were subsequently taken at various locations on the polished walls of the samples by a scanning microscope in BSE (backscattered electron) mode.

The raw images thus obtained were processed by a known technique for thresholding of the porosity, in such a manner that the noise pixels, in other words those pixels not corresponding to true porosity of the material, were eliminated from the photograph.

The series of images thus obtained was subsequently processed by the method of morphological erosion, the structuring element chosen being a disk of fixed radius and such as reported in table 2. This technique has the advantage of isolating regions of porosity and of highlighting the regularity, the continuity and the uniformity of the microstructure of the material forming said wall.

The erosion technique is known in the field relating to image analysis as a mathematical morphology tool. By way of example, the publication "Précis d'analyse d'images, M. Coster & JL. Chermant, CNRS Press, Paris (1989)—pages 72 to 74" may be mentioned, which describes the principle of such a method.

On a given series of images, obtained by the erosion method, the number, the mean area and the cumulative area of the residual regions, in other words after erosion, were determined by labeling according to techniques well known in the prior art and by means of the software application Visilog® marketed by the company Noesis.

The main analysis and evaluation data obtained for the specimens 2 to 5, representative of the full set of results obtained, are reported in table 2.

Various parts of the walls of the filter in the example 5 were processed by the erosion method while varying the dimensions of the structuring disk according to values of 30 μm (example 5a), 40 μm (example 5b) and 60 μm (example 5c).

In table 2, the reported values of the number of residual regions, the mean area of the regions and the cumulative area of the regions correspond to an average of said values, calculated from a series of 10 SEM images (BSE mode) of the wall surface, taken in various positions.

TABLE 2

|  |  | Examples | | | | | | |
| --- | --- | --- | --- | --- | --- | --- | --- | --- |
|  |  | 1 | 2 | 3 | 4 | 5a | 5b | 5c |
| Structural data/ Porosimetry | Nature of the substrate material | SiC | SiC | SiC | SiC | SiC | | |
|  | Open porosity | 35 | 42 | 47.5 | 52 | 47 | | |
|  | Median pore diameter ($\mu$m) | 9.1 | 12.0 | 13.5 | 16.0 | 14.0 | | |
| Wall surface data | Diameter of the disk forming the structuring element ($\mu$m) | 40 | 40 | 60 | 40 | 30 | 40 | 60 |
|  | Ratio $\frac{\text{disk diameter}}{\text{median pore diameter}}$ | 4.4 | 3.3 | 4.5 | 2.5 | 2.2 | 2.9 | 4.4 |
|  | Number of residual regions/mm$^2$ of wall* | <10 | 28 | 108 | 15 | 105 | 36 | 2 |
|  | Mean area of regions ($\mu$m$^2$/mm$^2$ of wall)* | 40 | 95 | 425 | 86 | 175 | 130 | 51 |
|  | Cumulative area of regions ($\mu$m$^2$/mm$^2$ of wall)* | 300 | 760 | 10,500 | 1,473 | 10,500 | 3500 | 72 |
| Filter evaluation tests | Soot deposition time (minutes) | 2.5 | 4.1 | 10.5 | 9 | 5.9 | | |
|  | Pressure drop (pascals) | 20 | 17 | 15 | 14 | 16 | | |
|  | Thermomechanical resistance | No cracks | No cracks | No cracks | A few micro-cracks | No cracks | | |

*Average values over a series of 10 different images.

The analysis in table 2 shows a surprising correlation between the microstructural characteristics of the filters deduced from the technique of morphological erosion and the results obtained in the various qualification tests for said filters. More particularly, it is observed that the best results and compromises in terms of soot deposits, of pressure drop and of thermomechanical resistance are obtained for the filtering structures made from R-SiC according to the present invention, such as are defined in the claims that follow.

The invention claimed is:

1. A method of making a filtering structure for a gas laden with particulates, said structure comprising a filtering part formed from a porous ceramic material and comprising at least one porous wall having pores and a microstructure, said method comprising processing a first image of the surface of the wall comprising morphologically eroding the first image with a structuring element in such a manner as to obtain a second characteristic image of the regularity and of the uniformity of the microstructure of said wall, wherein the structuring element is a disk chosen such that the ratio of its diameter to the median pore diameter is in the range between 1.5 and 5.

2. The method as claimed in claim 1, in which the dimensions and/or the morphology of the structuring element are chosen as a function of the median pore diameter, as measured by mercury porosimetry.

3. The method as claimed in claim 1, comprising:
preparing a section of wall,
performing an image acquisition by means of a scanning electron microscope (SEM),
processing the raw images by a thresholding technique in order to obtain digitized images,
processing the digitized images using the morphological erosion technique with a structuring element adapted to the median pore size of the filter,
characterizing the remaining regions of porosity, and
selecting the filtering structures on the basis of at least the following criteria:
a) the number of residual regions remaining after erosion,
b) the cumulative area of said regions, and
c) the mean area of said regions.

4. The method as claimed in claim 1, in which the porous material is chosen from the group consisting of cordierite, alumina, mullite, silicon nitride, silicon carbide and silicon/silicon carbide mixtures.

5. The method as claimed in claim 1, in which said walls exhibit an open porosity in the range between 30 and 60%, and a median pore diameter in the range between 8 and 30 $\mu$m.

6. The method as claimed in claim 1, wherein the structuring element is a disk chosen such that the ratio of its diameter to the median pore diameter is in the range between 1.5 and 5.

7. The method as claimed in claim 1, in which said walls exhibit an open porosity in the range between 40 and 53%, and a median pore diameter in the range between 8 and 30 $\mu$m.

8. The method as claimed in claim 1, in which said walls exhibit an open porosity in the range between 44 and 50%, and a median pore diameter in the range between 8 and 30 $\mu$m.

9. The method as claimed in claim 1, in which said walls exhibit an open porosity in the range between 30 and 60%, and a median pore diameter in the range between 9 and 25 $\mu$m.

10. The method as claimed in claim 1, in which said walls exhibit an open porosity in the range between 40 and 53%, and a median pore diameter in the range between 9 and 25 $\mu$m.

11. The method as claimed in claim 1, in which said walls exhibit an open porosity in the range between 44 and 50%, and a median pore diameter in the range between 9 and 25 $\mu$m.

12. The method as claimed in claim 1, in which said walls exhibit an open porosity in the range between 30 and 60%, and a median pore diameter in the range between 10 and 18 $\mu$m.

13. The method as claimed in claim 1, in which said walls exhibit an open porosity in the range between 40 and 53%, and a median pore diameter in the range between 10 and 18 $\mu$m.

14. The method as claimed in claim 1, in which said walls exhibit an open porosity in the range between 44 and 50%, and a median pore diameter in the range between 10 and 18 $\mu$m.

* * * * *

UNITED STATES PATENT AND TRADEMARK OFFICE
CERTIFICATE OF CORRECTION

PATENT NO.        : 8,066,798 B2                                          Page 1 of 1
APPLICATION NO.   : 12/095071
DATED             : November 29, 2011
INVENTOR(S)       : Celine Wiss et al.

It is certified that error appears in the above-identified patent and that said Letters Patent is hereby corrected as shown below:

On the title page, Item (73), the Assignee's name is incorrect. Item (73) should read:

-- (73) Assignee: Saint-Gobain Centre de Recherches et d'Etudes Europeen, Courbevoie (FR) --

Signed and Sealed this
Seventeenth Day of January, 2012

David J. Kappos
*Director of the United States Patent and Trademark Office*